United States Patent [19]

Manella

[11] Patent Number: 5,081,697
[45] Date of Patent: Jan. 14, 1992

[54] CONTAINER AND APPARATUS FOR WARMING OF INFUSION LIQUID AND TRANSFUSION LIQUID

[75] Inventor: Paul Manella, Dübendorf, Switzerland

[73] Assignee: Doltron AG, Uster, Switzerland

[21] Appl. No.: 315,122

[22] Filed: Feb. 24, 1989

[30] Foreign Application Priority Data

Mar. 8, 1988 [CH] Switzerland ............................ 863/88

[51] Int. Cl.⁵ ............................................. H05B 1/02
[52] U.S. Cl. .................................... 392/496; 392/481
[58] Field of Search .............. 219/302, 303, 304, 400; 73/23.1; 604/113, 114; 248/49, 68.1, 75, 79, 89; 165/163; 392/470, 480, 481, 482, 484, 496

[56] References Cited

U.S. PATENT DOCUMENTS

| | | | |
|---|---|---|---|
| 916,936 | 3/1909 | Taylor | 248/49 |
| 2,987,604 | 6/1961 | Swoyer | 393/495 |
| 3,595,309 | 7/1971 | Hawkins | 165/163 |
| 4,114,686 | 9/1978 | Mueller et al. | 165/163 |
| 4,420,679 | 12/1983 | Howe | 73/23.1 |
| 4,556,168 | 12/1985 | Romanow et al. | 392/482 |
| 4,680,445 | 7/1987 | Ogawa | 604/114 |
| 4,707,587 | 11/1987 | Greenblatt | 219/302 |

FOREIGN PATENT DOCUMENTS 1185964 4/1985 Canada ............................ 165/163

OTHER PUBLICATIONS

"A Review of Blood Warmers for Massive Transfusion" by Russell, Anaethesia and Intensive Care, vol. II, No. 2, 05/1974, pp. 109-130.

Primary Examiner—Geoffrey S. Evans
Attorney, Agent, or Firm—Charles A. Brown

[57] ABSTRACT

The container consists of a hose wound to four spiral coils and of a holding device for fixing the spiral coils parallel and spaced to each other, such that the individual spiral coils are substantially to be subjected from all sides with a heating medium. The apparatus includes a source of hot air into which the container is insertable. The temperature of the heating air is regulated by a measuring device and a controlling device. By using the heating air, an effective heating of the infusion liquid and the transfusion liquid is achieved, and a simple handling is possible without dripping bags.

7 Claims, 8 Drawing Sheets

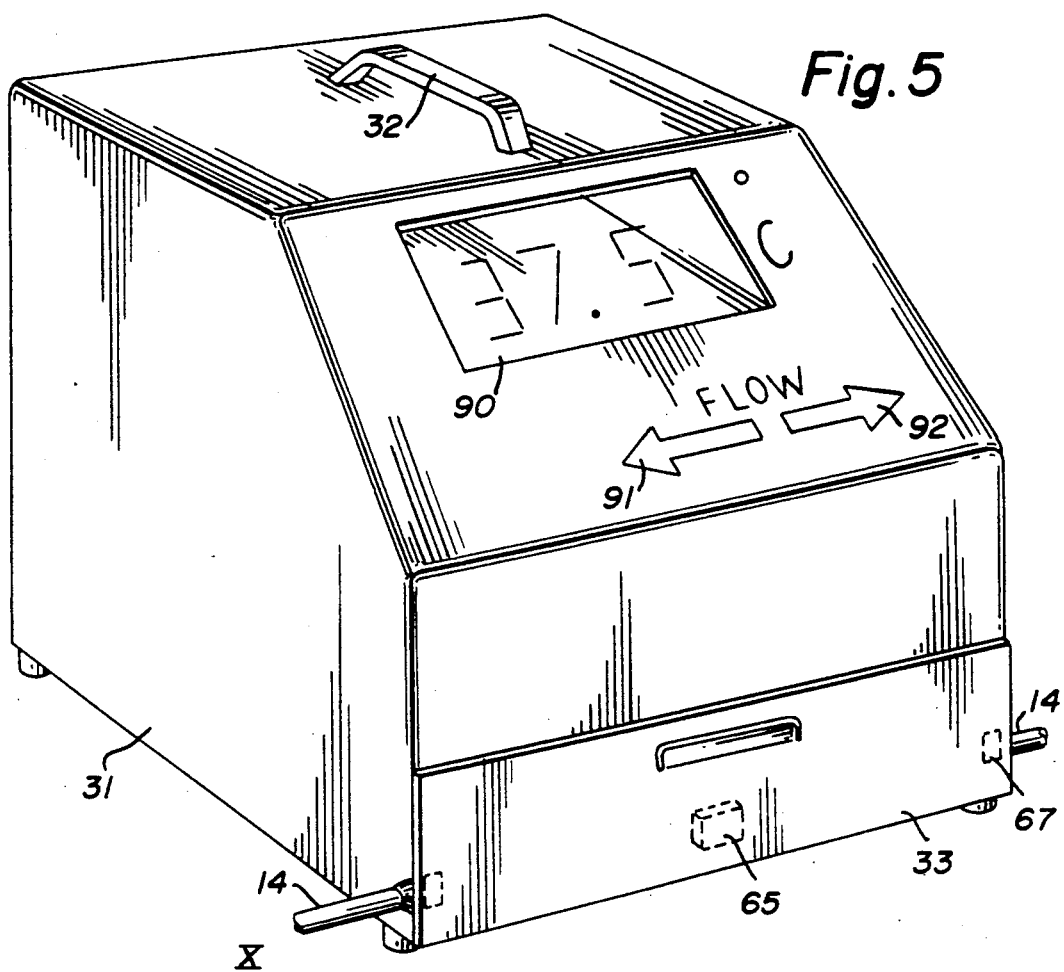
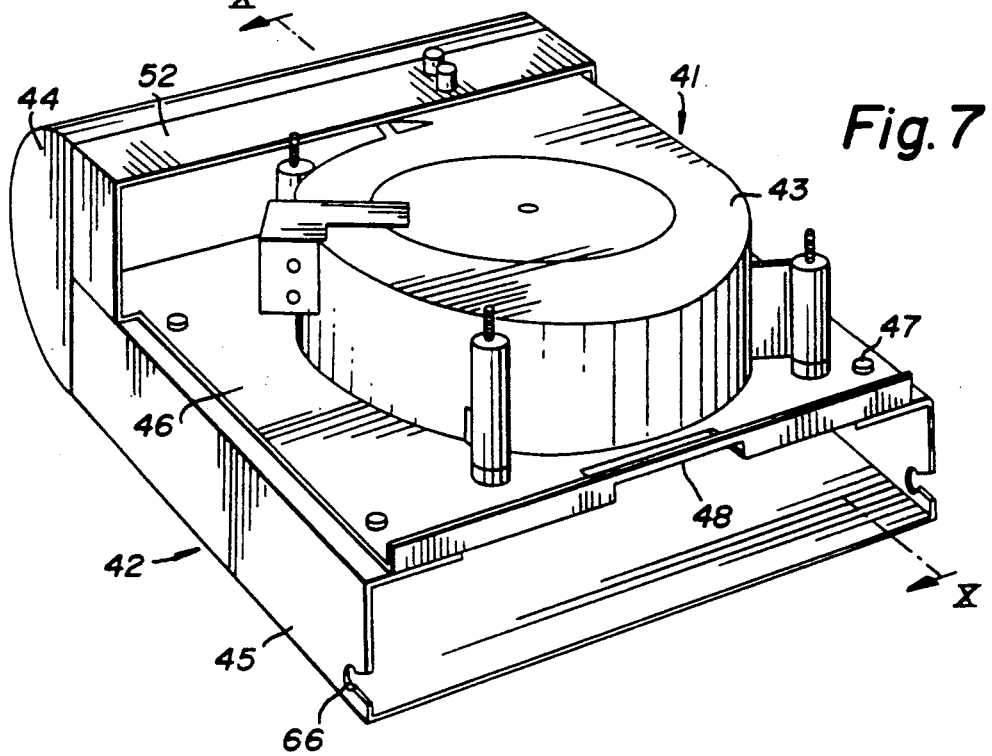

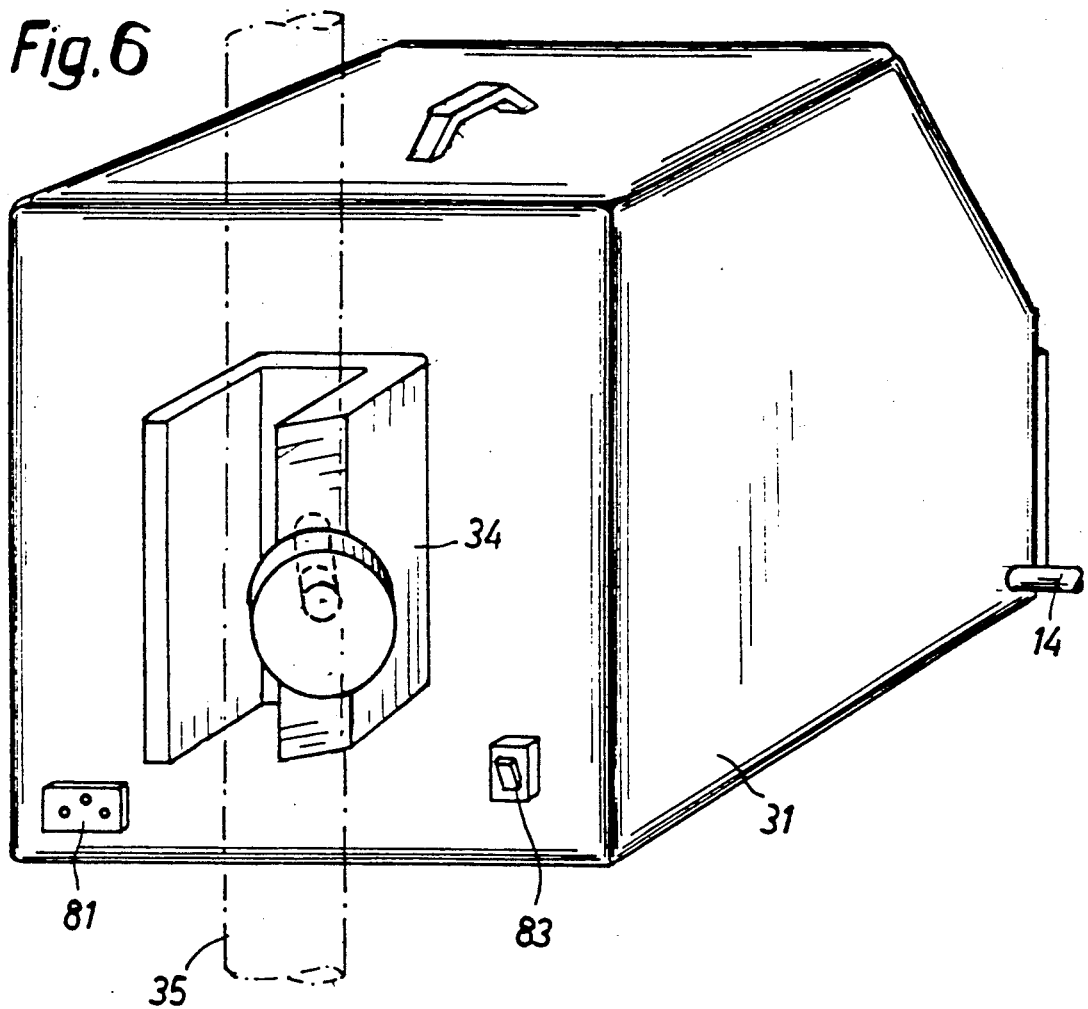

CONTAINER AND APPARATUS FOR WARMING OF INFUSION LIQUID AND TRANSFUSION LIQUID

BACKGROUND OF THE INVENTION

1. Field of The Invention

The present invention relates to a container for warming of infusion liquid and transfusion liquid and to an apparatus provided with such a container in order to warm physiological fluids.

2. Description of The Prior Art

Different embodiments of instruments and blood warmers are known. These embodiments are described in the essay "A Review of Blood Warmers for Massive Transfusion" by W. J. Russell, Anaesthesia and Intensive Care, Vol. II, No. 2, May 1974.

Essentially these embodiments can be divided into four groups.

1. Warming of the whole contents of a bag or of a bottle in a bucket of water of 37° C. or in a microwave oven, warming the liquid to a suitable temperature by means of high frequency electromagnetic oscillation. The warming before infusion has drawbacks, namely that it needs a relatively long time period to warm a bottle of blood;

the liquid will be partly cooled down during infusion;

an unmovable and much space-using apparatus has to be provided in the operating theatre when using a microwave oven;

a monitoring of temperature of the warmed liquid is not possible; and a determination of the temperature by means of empirical data is difficult.

2. Warming during infusion or transfusion wherein the liquid, for example blood, flows through a hose section conducted through water. This warming during infusion is commonly used. A hose up to 10 meters is somehow wound up, conducted through a bath of water and warms therefore the liquid up to the necessary 37° C.

It is a drawback that the inevitably open bath of water warmed up to 37° C. develops strong bacterial cultures and beside the sterility also the relative unmovableness, that is, the overflow of the water during hectic transport of the patient is a problem. Additionally it is not advantageous to handle wet and dripping instruments in the vicinity of the area of operation.

3. A hose to be wound around a warmed cylinder of aluminium or to be threaded in grooves. The drawbacks of this embodiment are a low effectiveness due to the commonly poor contact to hoses having a major thickness, a relatively long time period for warming due to said thickness, and a very long hose is necessary in order to avoid a thermodynamical shock in the patient by hypothermia.

4. A thin-walled bag having instruments connected thereto is disposed between a pair of heating plates for warming of the liquid flowing therethrough. This embodiment has the drawbacks that a bag with instruments is very expensive and that a high volume of liquid is necessary. This system will be very bulky due to the large surface necessary for an effective warming, as lack of space exists in the space for the nursing care of patients.

OBJECTS OF THE INVENTION

Therefore, it is an object to provide a container and apparatus for warming of an infusion liquid and transfusion liquid for warming during infusion or transfusion.

Another object of the present invention is to provide a container and apparatus for warming of an infusion liquid or transfusion liquid, without an effective determination of temperature and warming of the liquid is performable due to dividing of a container into partial volumes.

A further object of the present invention is to provide a container and an apparatus for warming of an infusion liquid or transfusion liquid as aforesaid, wherein the container consists of several sections and the apparatus performs the warming in each unit.

Various other objects, advantages and features of the present invention will become readily apparent from the ensuing detailed description and novel features will be particularly pointed out in the appended claims.

SUMMARY OF THE INVENTION

In accordance with this invention at least two sections are provided, which units are disposed superposed and spaced to each other such that the temperature of each sections is measurable and the compartments are in contact substantially from all sides with a heating medium. The advantages to be achieved are to be seen in that a number of partial volumes are combined to a possible large volume having a large surface in a single space and that the partial volumes are individually measurable.

For one embodiment the container consists of a hose and the sections are spiral coils. The following advantages result, in that the container is divisible in a plurality of individual partial volumes, each is a spiral coil, since the hose is a standard hose, for which the corresponding test certificate is on hand the container must not be subject to further tests.

An apparatus according to the invention is characterized by a container having at least two sections superposed and spaced to each other, such that the temperature of each section is measurable and the sections are in contact from all sides with a heating medium, a source of heating air to admit said container with heating air, a temperature measuring device with which the sections of the container are contactable to measure the temperature in said container, and a control device to control the source of heating air in response to the measured temperature.

The advantages of the apparatus are to be essentially seen in that the sections are individually and uniformly admitted with warm air and a quick regulation of temperature is achieved by the warm air.

The above and other objects, features and advantages of the present invention will become readily apparent from the following detailed description, which is to be read in connection with the accompanying drawings.

BRIEF DESCRIPTION OF THE DRAWINGS

FIG. 5 is a perspective view of an embodiment of an inventive blood warmer.

FIG. 6 is a perspective view of the blood warmer shown in FIG. 5, which shows the rear side of the apparatus.

FIG. 7 is a perspective view of an embodiment of a source of heating air of the blood warmer of FIG. 5.

DESCRIPTION OF THE PREFERRED EMBODIMENT

Figure 1:
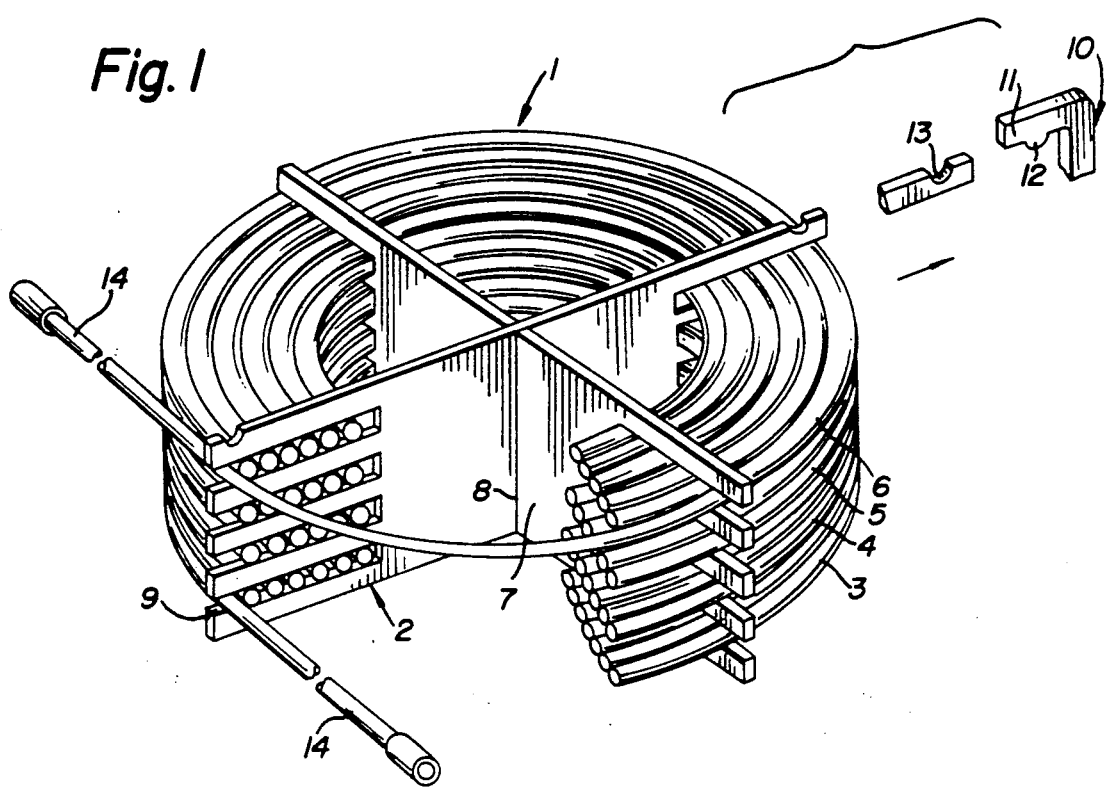
FIG. 1 is a perspective view of a preferred embodiment of an inventive container.

In the embodiment shown in FIG. 1, the container 1 substantially consists of a plastic hose and holding means 2. The container 1 forms four sections wound as spiral coils 3,4,5,6 and individually held in the holding means 2. The holding means 2 includes two elongated plates 7, identically formed and joined together to a crossbar. For this purpose the plates 7 are provided with a slit 8. In each case four slits 9 are formed in the narrow sides of the plates 7, said slits 9 being formed parallel and spaced to each other in the longitudinal direction of the plate 7. The holding means further includes four clamps 10, placed on the free ends of the plates 7. The clamp 10 is U-shaped and includes in each case a bulge 12 on the legs 11, said bulge 12 engaging into a recess 13 of the plate 7 for holding the clamp 10.

Figure 2A:
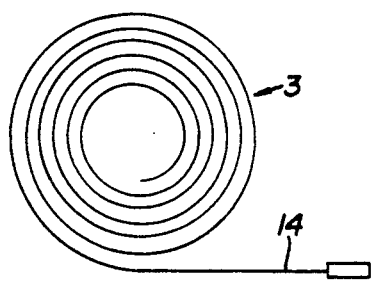
FIGS. 2A-2D are schematical drawings of the individual spiral coils of the container according to FIG. 1.
Figure 2B:
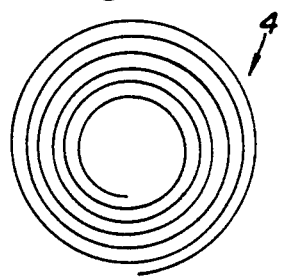
Figure 2C:
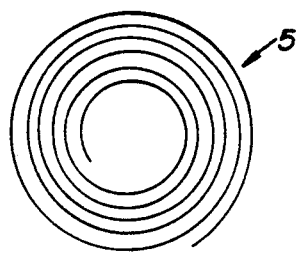
Figure 2D:
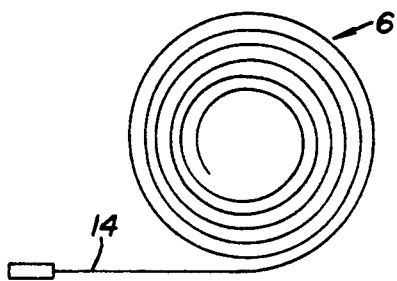

To manufacture the container shown in FIG. 1, the hose is wound to four spiral coils 3,4,5,6 according to FIGS. 2A–2D, whereby FIG. 2A shows the wound direction of the spiral coil 3, FIG. 2B shows the wound direction of the spiral coil 4, FIG. 2C shows the wound direction of the spiral coil 5 and FIG. 2D shows the wound direction of the spiral coil 6.

As can be seen from these figures, the spiral coils 3,4,5,6 run from the inside to the outside. Whilst the spiral coil 3 is wound counterclockwise, the other three spiral coils 4, 5 and 6 are wound in the opposite direction. In order to achieve this, firstly the spiral coil 4 is wound from inside to outside onto the holding means 2. Then, the spiral coil 5 can be wound in that the hose is inserted into the next slot 9 provided above and the hose is then wound from the inside to the outside onto the holding means 2. In order to wind the spiral coil 6, it is proceeded like in the spiral coil 5. Finally, the spiral coil 3 can be wound from inside to outside. It is observed that two sections of the hose 14 for donor and receiver are present for the winding.

Standard connections for instruments are provided at the ends of the hose sections 14 (not shown).

Figure 3:
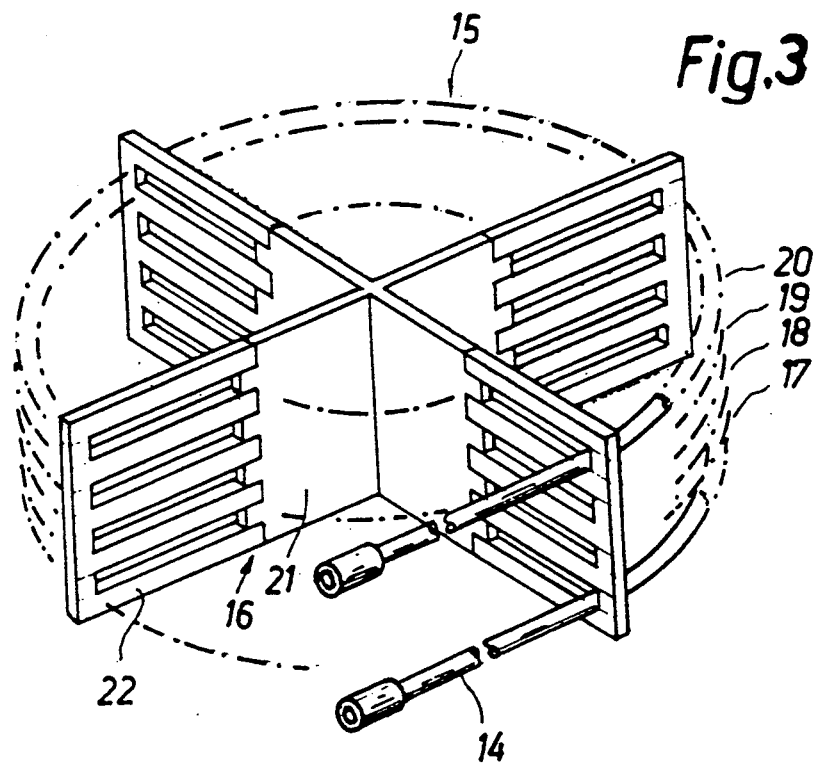
FIG. 3 is a perspective view of another embodiment of the container.
Figure 4A:
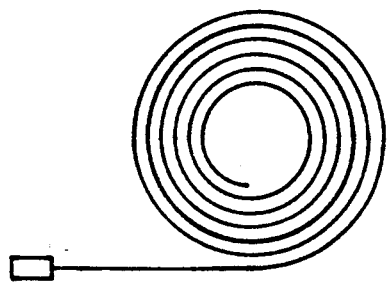
FIGS. 4A–4D are schematical drawings of the individual spiral coils of the container according to FIG. 3.
Figure 4B:
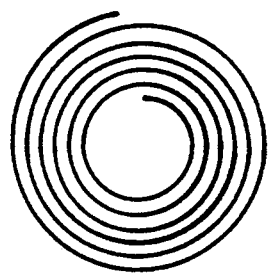
Figure 4C:
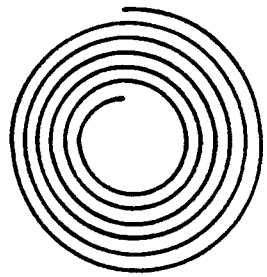
Figure 4D:
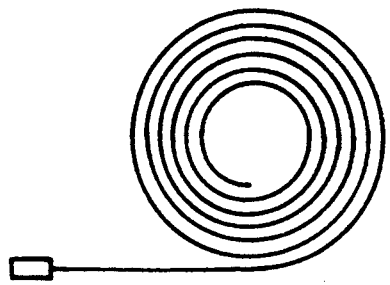

The container 15 shown in FIG. 3 consists of four spiral coils 17, 18, 19, 20 and a holding means 16.

The holding means 16 includes a star 21 and four combs 22, which are mountable on the star and which hold the spiral coils 17 to 20.

As FIGS. 4A–4D show, the container 15 is different from that shown in FIG. 1 in that the spiral coils 17–20 are alternately wound from the inside to the outside.

The foregoing described containers are used together with a blood warmer. An embodiment of such a blood warmer is shown in FIGS. 5–13.

The blood warmer is constructed as a portable apparatus and comprises a housing 31 having a handle 32. Display means 90–92 are provided on the front side, which means will be described later on. Further, a lid 33 is provided on the front side in order to insert a container (FIG. 5). Means 34 for fixing the blood warmer, eg to a standpipe 35 are disposed on the rear side. Furthermore, a power supply plug 81, and a main switch 83 are provided on the rear side, which will be described later. Two hose sections 14 protrude from the housing 31 in the front region on both sides when a container is inserted in the blood warmer.

Figure 10:
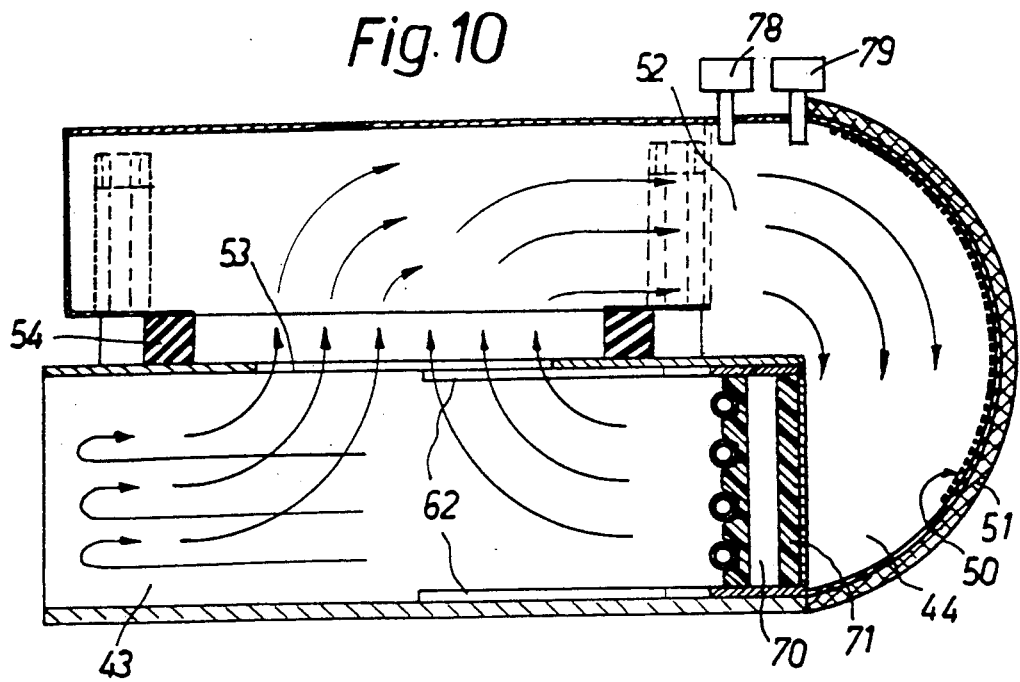
FIG. 10 is a sectional view along the line X—X in FIG. 7.
Figure 12:
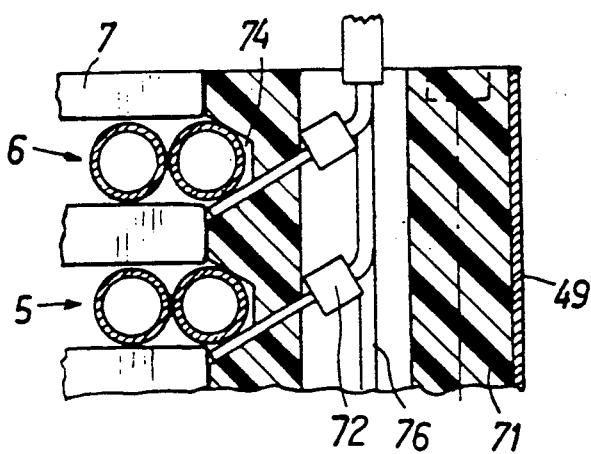
FIG. 12 is a sectional view along the line XII—XII in FIG. 11.
Figure 11:
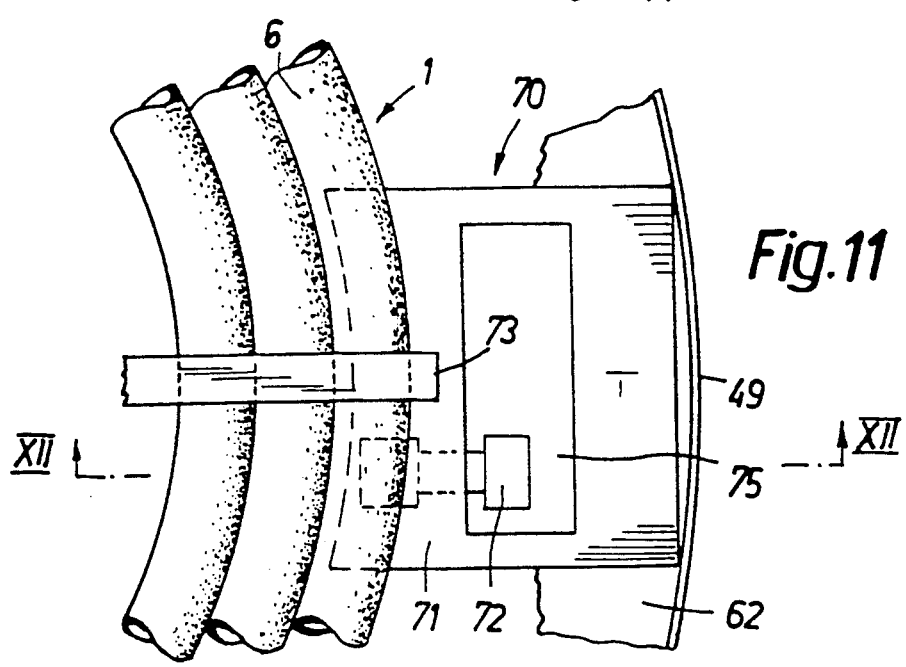
FIG. 11 is a view in the direction of the arrow XI in FIG. 9.

A source of heat air 41, a temperature measuring device 70 and a control device 80 are disposed in the housing 31. FIG. 7 shows a perspective view of the source of heating air 41 and FIG. 10 shows a section of the source of heating air 41. This source 41 is constructed as heating device by circulating air. The heating device includes a chassis 42, forming the input unit for a container, a fan 43 supplying air and a heating channel 44 heating the air. The chassis 42 comprises a bottom part 45 and a cover plate 46 mounted to the bottom part 45 by means of screws 47. The cover plate 46 forms simultaneously the hinge plate for the lid 33. Therefore, the hinge plate includes a recess 48, which is provided at that side of the chassis 42 forming the inlet for the container. A baffle 49 is disposed in the chassis 42 on the side forming the air inlet, such that two identical openings of air-supply are formed. The inlet of the fan 43 is mounted onto the cover plate 46. The outlet of the fan 43 is connected with the chassis 42 by the heating channel 44. The heating channel 44 is provided with a heating element 50 on the inner side and with an isolating layer 51 on the outer side (FIG. 10). As FIG. 7 shows, the heating channel 44 is connected to the outlet of the fan 43 via a chute 52. Moreover, the chute 52 and the cover plate 46 are connected together. The cover plate 46 has a hole 53 facing the inlet of the fan 43. Further, a seal member 54 is mounted between fan 43 and cover plate 46 (FIG. 10).

Figure 8:
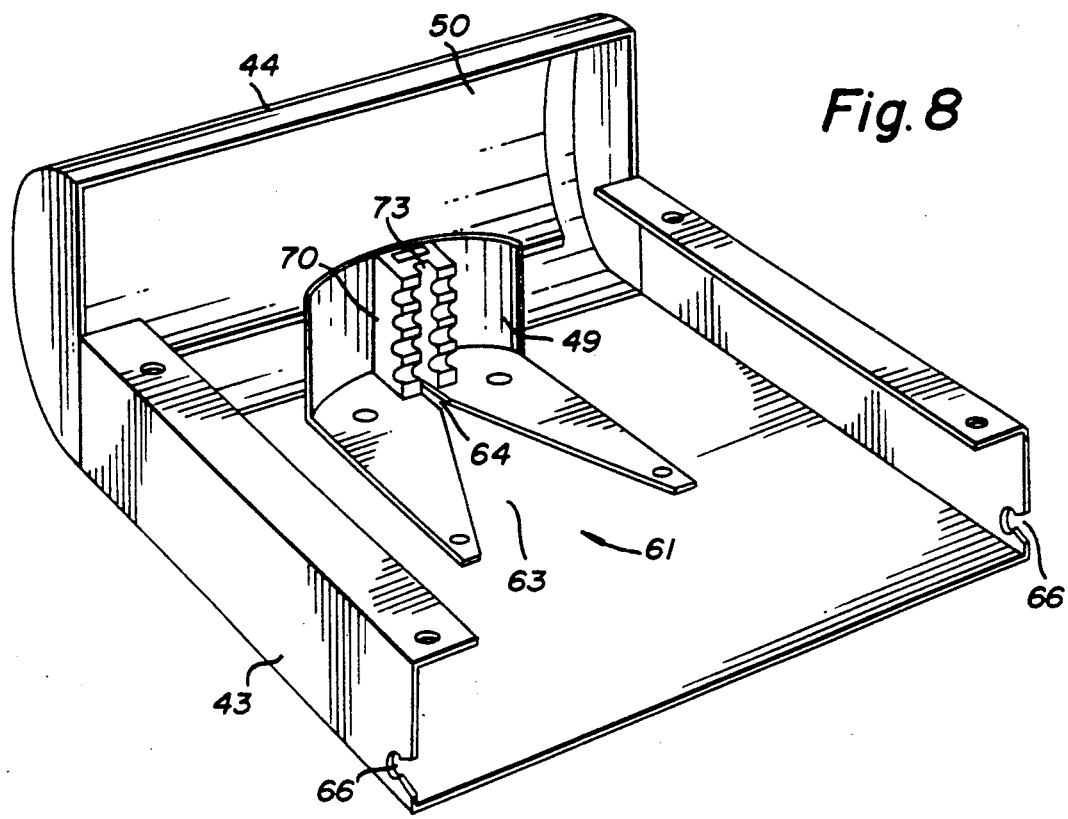
FIG. 8 is a perspective view of a part of the source of heating air of FIG. 7.
Figure 9:
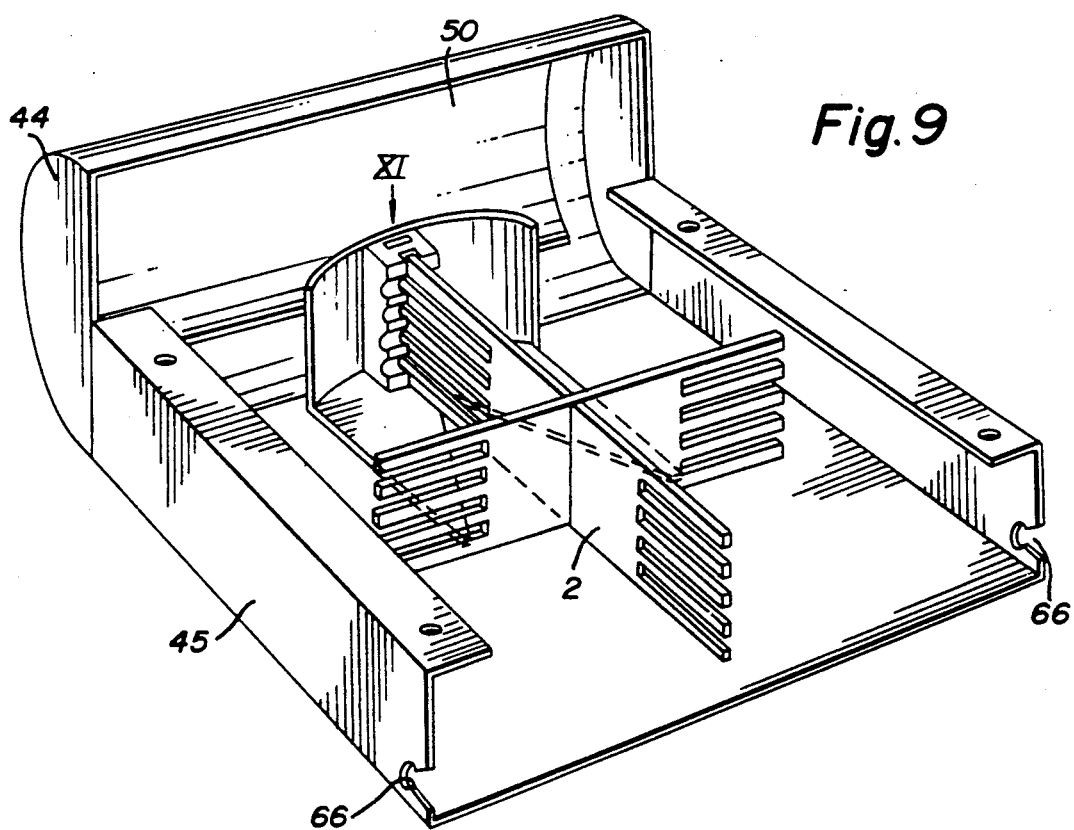
FIG. 9 is the same view as in FIG. 8, wherein the arrangement of the container of FIG. 1 is shown with the aid of one of its parts.

As particularly obvious from FIGS. 8 and 9, an alignment device 61 is provided in the chassis 42 of the oven 41 for aligning a container regarding the heating air flow and the temperature measuring device 70. The aligning device 61 includes two guide plates 62 mounted opposed to one another on the bottom part 45 and the cover plate 46, respectively. The guide plates 62 have a V-shaped cutout 63 and adjacent thereto a U-shaped notch 64, into which the holding device 2 of the container (FIG. 1) is insertable, as shown in FIG. 9. The aligning device 61 further comprises a pressure part 65 which is fixed on the inner side of the lid 33. The pressure part 65 can be brought in contact with the holding device of the container in order to keep the container within the aligning device 61. Two openings 66 are provided in order to bring out two hose sections 14 from the blood warmer (FIG. 9). The openings 66 are in the form of a keyhole and are arranged in the housing 31 in the region of the front side and in the side walls of the chassis 42 such that the hose sections 14 can be inserted when the lid 33 is opened. Seal members 67 are disposed on the inner side of the lid 33, sealing the openings 66 when the lid 33 is closed.

The temperature measuring device 70 includes a holder 71 disposed between the guide plates 62 in the chassis 42 (FIG. 10) and four temperature sensors 72, which can be brought in contact with the individual spiral coils of a container. The holder 71 consisting of plastic includes a slit 73, into which the holding device 2 of a container is insertable (FIGS. 8 and 9). The holder 71 has four recesses 74 which are formed and superposed such that a section of the outermost winding of the spiral coils 3, 4, 5, 6 in each case extends into a recess 74. The recess 74 has a V-shaped cross-section, in order to ensure that the hose section is adjacent at least at the walls of the recess 74. This is used for the temperature measuring in that the temperature sensors 72 are disposed such in the holder 71 that a section of these temperature sensors 72 represents a wall of the recess 74. A hole 75 is formed in the holder 71 through which the connecting wires 76 for the temperature sensors are passed in order to connect the temperature sensors 72 with the control device.

In addition to the four temperature sensors 72 for the container 1, there are provided also a temperature sensor 78 for the limit value of temperature and a temperature sensor 79 for monitoring of the fan 43. These temperature sensors 78 and 79 are disposed between fan 43 and heating channel 44 (FIG. 10). Further, a door switch is mounted in the region of the lid 33, which switch serves as security switch.

Figure 13:
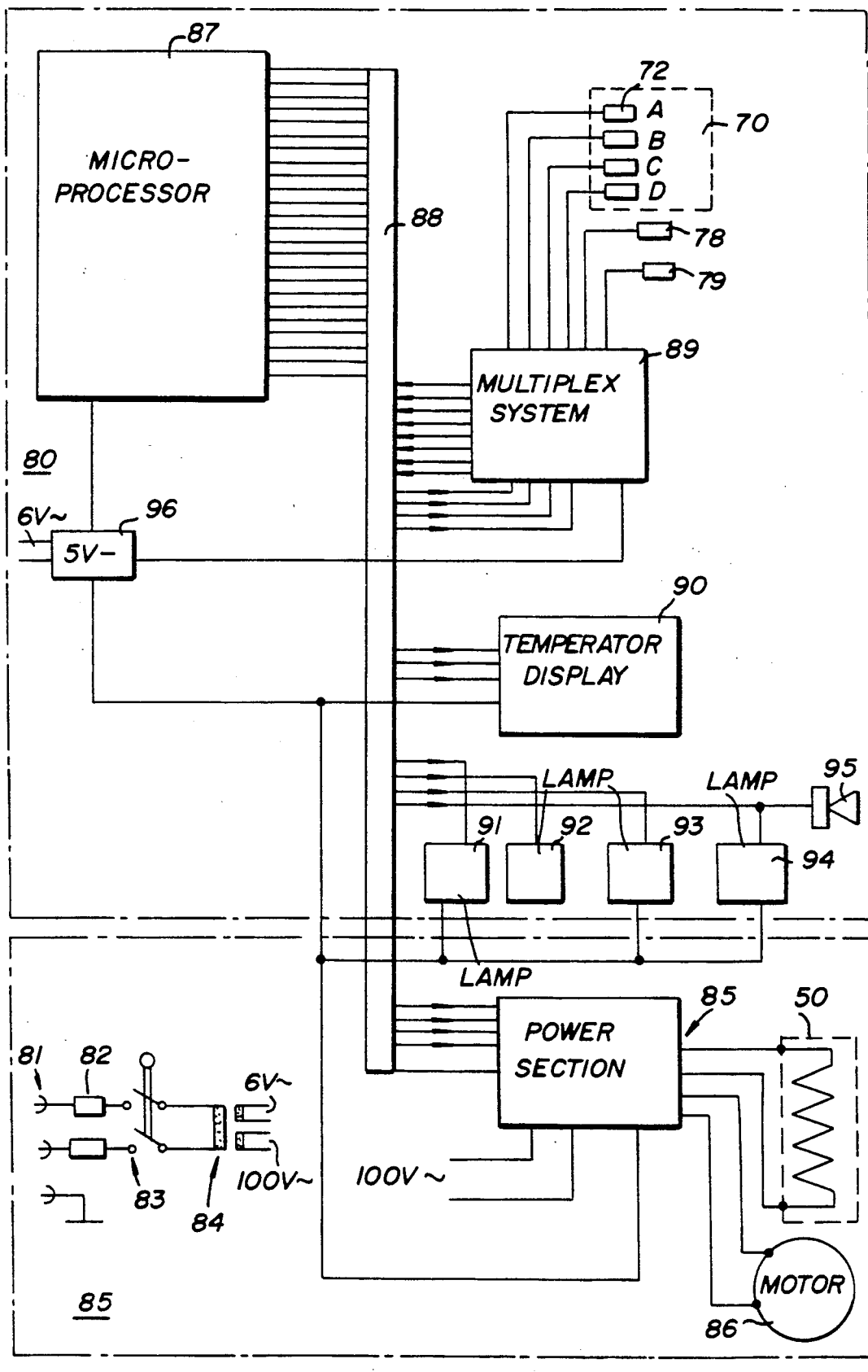
FIG. 13 is a block diagram of the control device for the blood warmer of FIG. 5.
Figure 14:
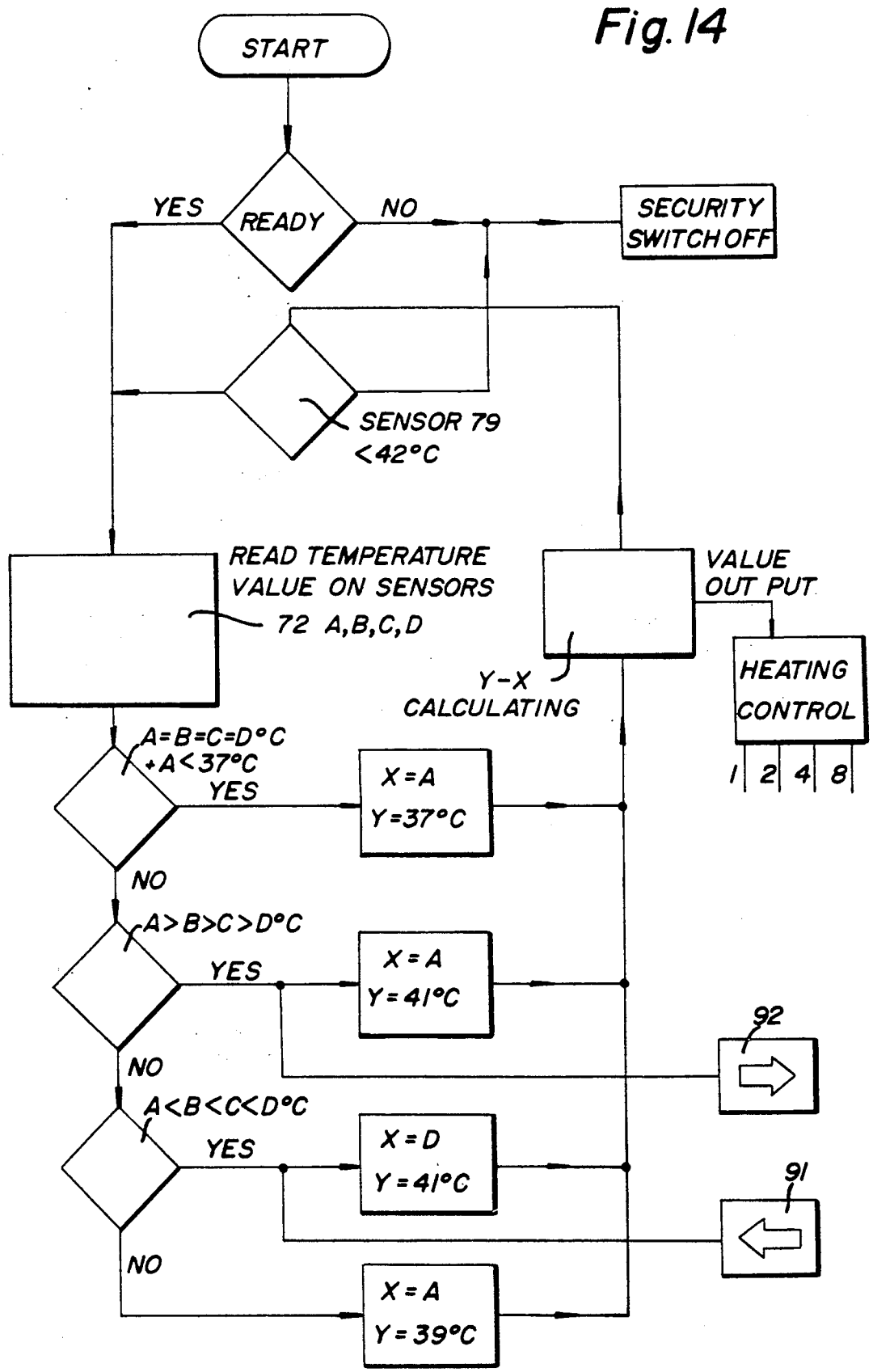
FIG. 14 is a flow chart of the regulation of temperature for the blood warmer.

As mentioned, the blood warmer has a control device, shown in FIG. 13. The blood warmer can be connected to the power supply through a plug 81. The plug 81 is connected with a power transformer 84 through fuses 82 and a main switch 83. The transformer 84 is provided with a tap for a-c voltage of 6 V and a tap for ac-voltage of 100 V. Ac-voltage of 100 V is supplied to the power section 85 of the control device. The power part comprises circuit elements for switching ON/OFF of the heating element 50 and the motor 86 of the fan. The power section 85 includes further a full-wave suppression circuitry connected to the heating element 50. The structure of the full-wave suppression circuitry is well known and therefore is not described in detail. However, it will be appreciated that 16 heating stages, i.e. 16 suppression stages are provided (Binary 4 Lines).

A microprocessor 87 is the main element of a control section of the control device. The microprocessor 87 is connected with a multiplex system 89, temperature indicating instrument 90, indicating lamps for the direction of the flow 91, 92, an indicating lamp 93 "heating", an indicating lamp 94 "warning", a buzzer 95 and the power section 85 via a data bus 88. In addition to the temperature sensors 72 for the individual spiral coils, and the temperature sensors 78 and 79, also the door switch 80 is connected to the multiplex system 89. A rectifier 96 supplies a dc-voltage of 5 V to the control section. The rectifier 96 is connected to the 6 V tap of the transformer 84.

According to their arrangement, the four temperature sensors 72 are additionally indicated from top to bottom with letters A, B, C and D.

In the following, an example of the temperature regulation with a blood warmer will be described.

The readiness for use is detected after turn on. This comprises among others testing of the temperature sensors 72A, 72B, 72C, 72D, 78 and 79. If one temperature sensor is defective, the blood warmer will be turned off and an alarm signal is given. Simultaneously with or subsequently to the detection of the readiness for use it will be observed whether the temperature measured by the temperature sensor is <42° C. If not, the blood warmer will be turned off. If the readiness of use is detected and the temperature measured by the temperature sensor 79 is <42° C., the temperature values of the temperature sensors 72 are scanned, namely in the order A, B, C, D, that is from top to bottom in the temperature measuring device 70. If the temperature sensors 72 measure the same values, and the value measured by the temperature sensor 72A amounts to <37° C., the temperature value. A measured by the temperature sensor 72A is set as operand X and a desired temperature of 37° C. preset in the microprocessor 87 is set as operand Y. Both operands are linked with each other and a corresponding value is applied to the control device for controlling of the heating element. The above mentioned case is a matter of starting of the blood warmer wherein the container will be preheated. The temperature sensors 72 measure different values when blood is flowing into the container. If it is detected that the value A measured by temperature sensor 72A is the highest value, this value A is set as operand X and a desired value of temperature of 41° C. given by microprocessor 87 is set as operand Y. These operands X, Y are linked to each other and a corresponding value for the controlling of the heating element is generated. In the above mentioned case the blood flows in the direction from the lowermost spiral coil 3 to the topmost spiral coil 6 through the container (FIG. 1). This will be indicated by the indicating instrument 92. If contrary to the above mentioned case it is ascertained that the value D measured by the temperature sensor 72D is the highest value, an analogue procedure is carried out, whereby it has to be considered that the blood flows in the opposite direction through the container, that is from the topmost spiral coil 6 to the lowermost spiral coil 3. This will be indicated by the indicating instrument 91.

If none of these conditions are ascertained, the value measured by the temperature sensor 72A is set as operand X and a desired value of 39° C. given by the microprocessor 87 is set as operand Y. These operands X, Y are linked and a corresponding value for controlling of the heating element is generated. For the sake of completeness, it will be appreciated that after linking of the operands X, Y, in each case a feedback signal is generated in order to maintain the procedure of temperature regulation.

I claim:

1. An apparatus for warming of transfusion medium or infusion medium, said apparatus comprising a container having at least two sections superposed and spaced to one another, wherein the temperature of each section is measured and the sections are on contact from all sides with a heating medium, a source of heating air to admit said container with heating air, a temperature measuring device with which the sections of the container is contacted to measure the temperature in the container, and a control device to control the source of heating air in response to the measured temperature, the source of heating air including a chassis for receiving of the container, a fan having an inlet and an outlet, the inlet of the fan is mounted to the chassis, and a heating channel having at least one heating element, with the heating element channel connecting the outlet of the fan with the chassis.

2. Apparatus according to claim 1, wherein a baffle is disposed in the region of the air inlet of the chassis to divide the stream of heating air.

3. Apparatus according to claim 1, wherein the chassis is provided with a register means to align the container with regard to the air stream and the temperature measuring device, and wherein a sealing unit is provided to support the container in the register means.

4. Appartus of claim 1, wherein the temperature measuring device includes temperature sensors, the number of which corresponds with the number of sections and which units are contactable with the temperature sensors to measure the temperature on each section.

5. Apparatus for warming of transfusion medium or infusion medium, comprising a container consisting of a hose and having four spiral coils superposed and spaced to each other, that the temperature of each spiral coil is measurable and the spiral coils are in contact from all sides with a heating medium,
- a source of heating air to heat said spiral coils with heating air,
- a temperature measuring device having temperature sensors disposed in a holding device such that one spiral coil in each case can be brought in contact with the corresponding temperature sensor to measure the temperature on each spiral coil, and
- a control device to control the source of heating air in response to a measured temperature of one of the four spiral coils.

6. Apparatus of claim 5, wherein said temperature sensors are connected with a circuitry to measure the gradual variation of temperature through spiral coils.

7. Apparatus of claim 5, wherein the source of heating air includes a heating element connected with a suppression circuit of the control device to control the heating power in response to the temperature measured on said spiral coils.

* * * * *